United States Patent
Akiyama et al.

(10) Patent No.: US 11,162,938 B2
(45) Date of Patent: Nov. 2, 2021

(54) MEMBRANE CARRIER, KIT FOR TESTING LIQUID SAMPLE USING SAME, AND MANUFACTURING METHOD THEREOF

(71) Applicant: Denka Company Limited, Tokyo (JP)

(72) Inventors: Yuto Akiyama, Machida (JP); Kenji Monden, Tokyo (JP)

(73) Assignee: Denka Company Limited, Tokyo (JP)

( * ) Notice: Subject to any disclaimer, the term of this patent is extended or adjusted under 35 U.S.C. 154(b) by 21 days.

(21) Appl. No.: 16/494,183

(22) PCT Filed: Mar. 28, 2018

(86) PCT No.: PCT/JP2018/012926
§ 371 (c)(1),
(2) Date: Sep. 13, 2019

(87) PCT Pub. No.: WO2018/181549
PCT Pub. Date: Oct. 4, 2018

(65) Prior Publication Data
US 2020/0011859 A1     Jan. 9, 2020

(30) Foreign Application Priority Data
Mar. 28, 2017 (JP) .............. JP2017-062948

(51) Int. Cl.
*G01N 33/543* (2006.01)
*G01N 21/78* (2006.01)

(52) U.S. Cl.
CPC .......... *G01N 33/543* (2013.01); *G01N 21/78* (2013.01)

(58) Field of Classification Search
CPC .............. G01N 33/543; G01N 21/78; G01N 33/54313; G01N 2021/7786; G01N 2021/6439; G01N 33/558; G01N 37/00
See application file for complete search history.

(56) References Cited

U.S. PATENT DOCUMENTS

| 5,458,852 A | 10/1995 | Buechler et al. |
| 7,824,611 B2 | 11/2010 | Buechler |
| 8,445,293 B2 | 5/2013 | Babu et al. |
| 2005/0136552 A1 | 6/2005 | Buechler |
| 2009/0111197 A1 | 4/2009 | Khan et al. |

(Continued)

FOREIGN PATENT DOCUMENTS

| EP | 2 835 645 | 2/2015 |
| JP | S63-014783 | 4/1988 |

(Continued)

OTHER PUBLICATIONS

Idegami Kotaro, Liquid Absorption Member and Vital Reaction Detecting System, translation of JP2013053897 (Year: 2013).*

(Continued)

*Primary Examiner* — Jennifer Wecker
*Assistant Examiner* — Jonathan Bortoli
(74) *Attorney, Agent, or Firm* — Leydig, Voit & Mayer, Ltd.

(57) ABSTRACT

The present invention provides a membrane carrier 3 comprising a flow path 2, wherein a microstructure is formed at a bottom of the flow path 2, and a particle to which an antibody or an antigen binds is arranged in at least a part on the flow path, the particle having a diameter of 500 nm or more and 100 μm or less.

7 Claims, 8 Drawing Sheets

(56) References Cited

U.S. PATENT DOCUMENTS

| | | | |
|---|---|---|---|
| 2010/0255512 A1 | 10/2010 | Wu et al. |
| 2011/0143450 A1 | 6/2011 | White |
| 2011/0284110 A1 | 11/2011 | Gagnon |
| 2012/0225496 A1 | 9/2012 | Yoshida |
| 2019/0329246 A1 | 10/2019 | Akiyama et al. |

FOREIGN PATENT DOCUMENTS

| | | |
|---|---|---|
| JP | H6-509424 | 10/1994 |
| JP | 2588174 | 3/1997 |
| JP | H10-123137 | 5/1998 |
| JP | 3513075 | 3/2004 |
| JP | 2005-077301 | 3/2005 |
| JP | 2007-024498 | 2/2007 |
| JP | 2009-241375 | 10/2009 |
| JP | 4597664 | 12/2010 |
| JP | 2012-002806 | 1/2012 |
| JP | 2012-505418 | 3/2012 |
| JP | 2012-524894 | 10/2012 |
| JP | 5147011 | 2/2013 |
| JP | 2013-053897 | 3/2013 |
| JP | 2013-507633 | 3/2013 |
| JP | 2013-113633 | 6/2013 |
| JP | 2013-148586 | 8/2013 |
| JP | 2014-062820 | 4/2014 |
| JP | 2014-081369 | 5/2014 |
| JP | 2014-098715 | 5/2014 |
| JP | 5609648 | 10/2014 |
| JP | 5799395 | 10/2015 |
| JP | 2016-011943 | 1/2016 |
| JP | 2017-040631 | 2/2017 |
| WO | WO 91/019980 | 12/1991 |
| WO | WO 93/024231 | 12/1993 |
| WO | WO 2003/103835 | 12/2003 |
| WO | WO 2009/096529 | 8/2009 |
| WO | WO 2010/061598 | 6/2010 |
| WO | WO 2010/122158 | 10/2010 |
| WO | WO 2011/045436 | 4/2011 |
| WO | WO 2011/062157 | 5/2011 |
| WO | WO 2016/051974 | 4/2016 |
| WO | WO 2016/098740 | 6/2016 |
| WO | WO 2017/217406 | 12/2017 |
| WO | WO 2018/181540 | 10/2018 |

OTHER PUBLICATIONS

International Preliminary Report on Patentability, dated Dec. 27, 2018, corresponding to International Application No. PCT/JP2017/021801 (filed Jun. 13, 2017), 16 pp.

International Preliminary Report on Patentability, dated Oct. 10, 2019, corresponding to International Application No. PCT/JP2018/012926 (filed Mar. 28, 2018), 8 pp.

International Preliminary Report on Patentability, dated Oct. 10, 2019, corresponding to International Application No. PCT/JP2018/012901 (filed Mar. 28, 2018), 9 pp.

Rivas, Lourdes (2014) "Improving Sensitivity of Gold Nanoparticle-Based Lateral Flow Assays by Using Wax-Printed Pillars as Delay Barriers of Microfluidics," Lab on a Chip, 14:4406-4414.

Search Report and Written Opinion, dated Jul. 18, 2017, corresponding to International Application No. PCT/JP2017/021801 (filed Jun. 13, 2017), 16 pp.

Search Report and Written Opinion, dated Jun. 26, 2018, corresponding to International Application No. PCT/JP2018/012926 (filed Mar. 28, 2018), 8 pp.

Search Report and Written Opinion, dated Jun. 26, 2018, corresponding to International Application No. PCT/JP2018/012901 (filed Mar. 28, 2018), 9 pp.

Extended European Search Report, dated Feb. 21, 2020, corresponding to European Application No. 18778273.5, 8 pp.

European Office Action, dated Sep. 24, 2020, corresponding to European Patent Application No. 18778273.5, 6 pp.

U.S. Appl. No. 16/309,877, filed Dec. 13, 2018.

U.S. Appl. No. 16/494,232, filed Sep. 13, 2019.

European Office Action, dated Mar. 23, 2021, corresponding to European Patent Application No. 18778273.5, 6 pp.

Japanese Office Action, dated Jul. 6, 2021, corresponding to Japanese Patent Application No. 2019-510020.

* cited by examiner

Fig.3
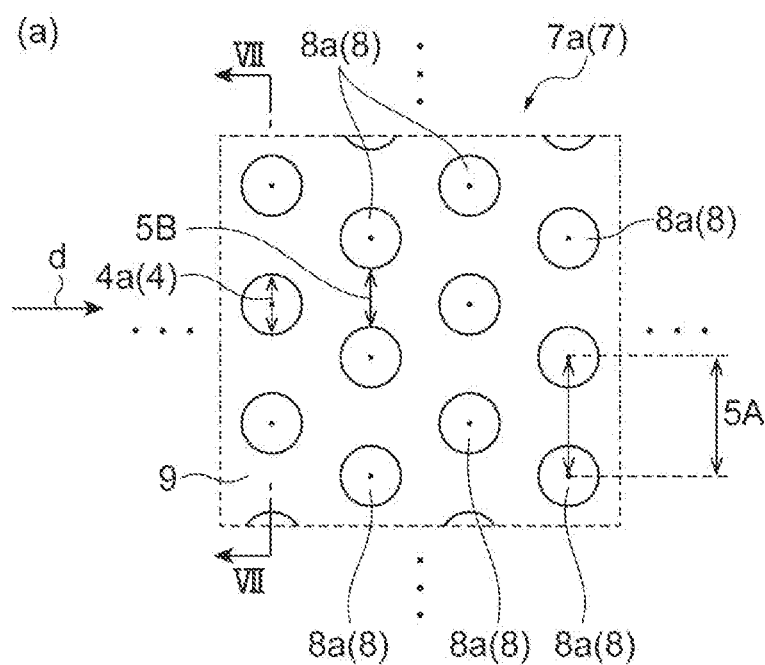
(a)
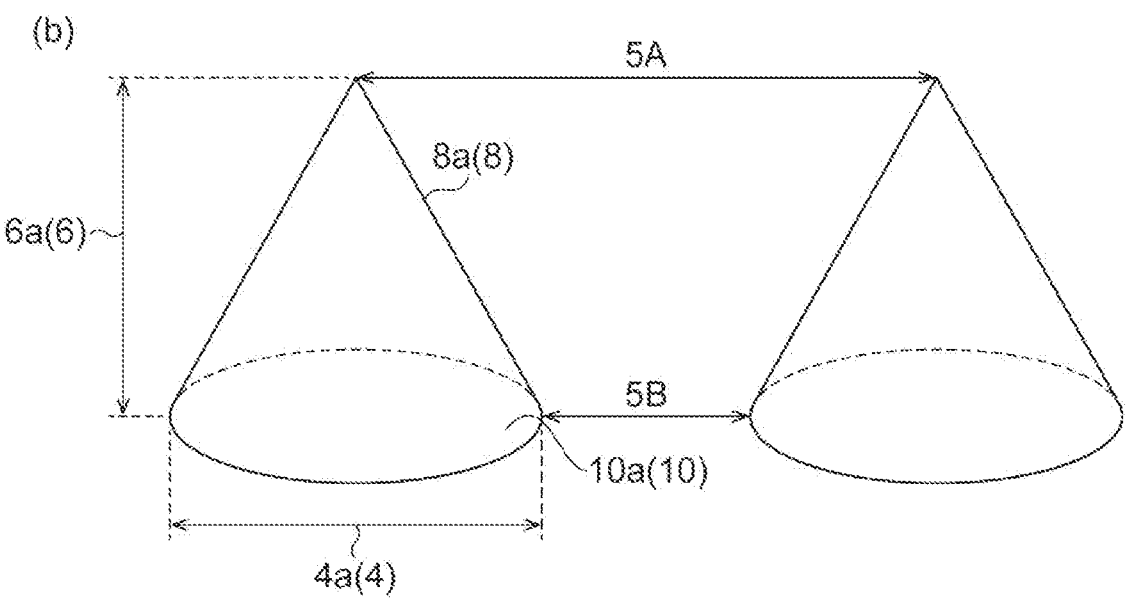
(b)

Fig.4
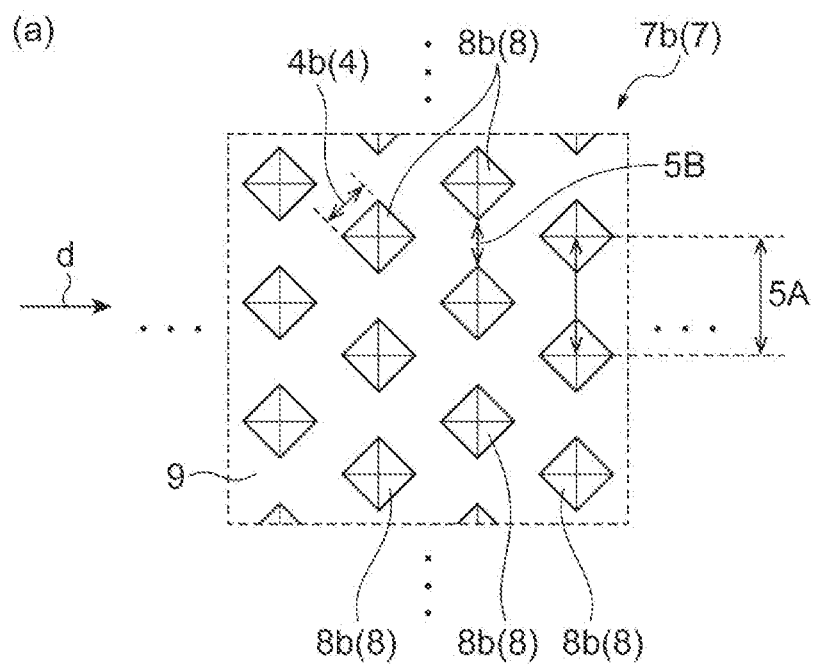
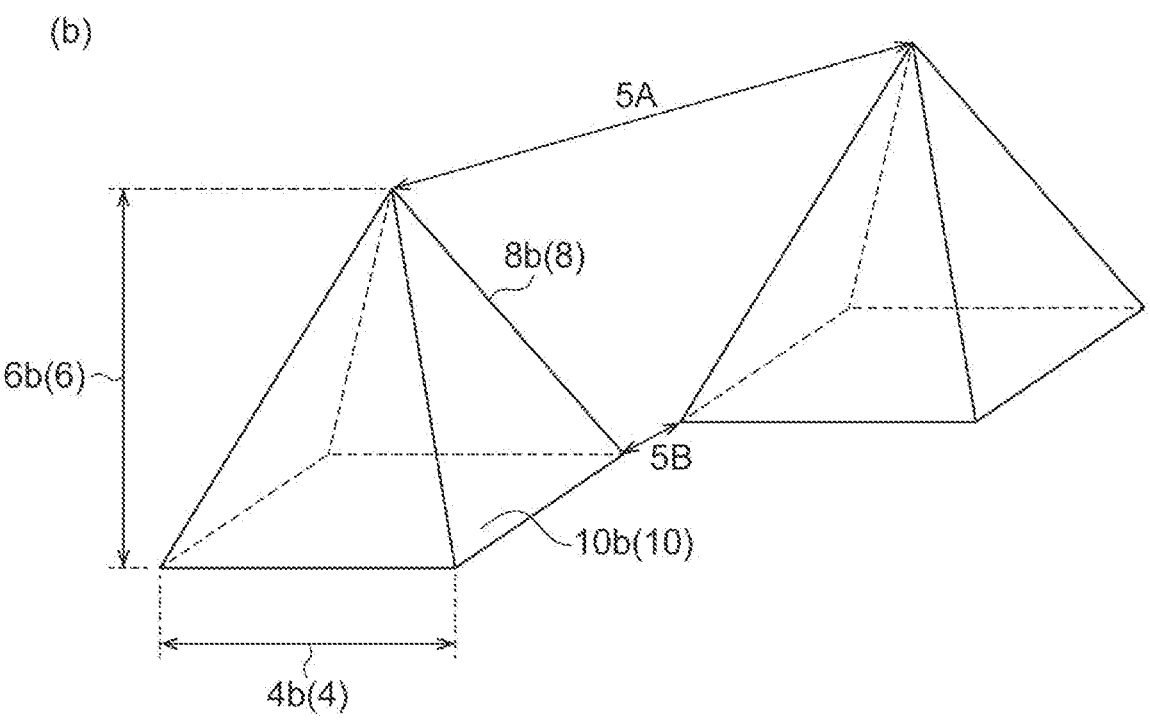

Fig.5
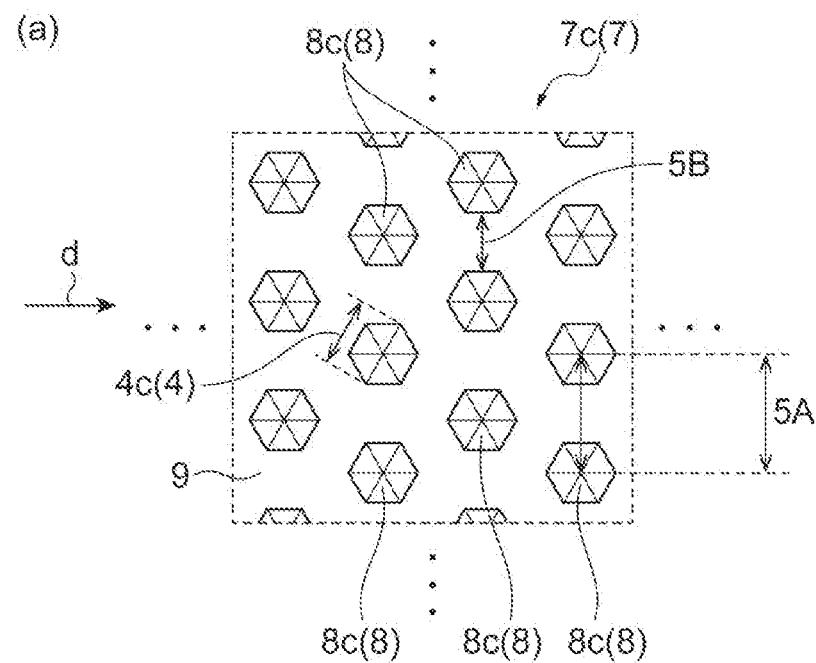
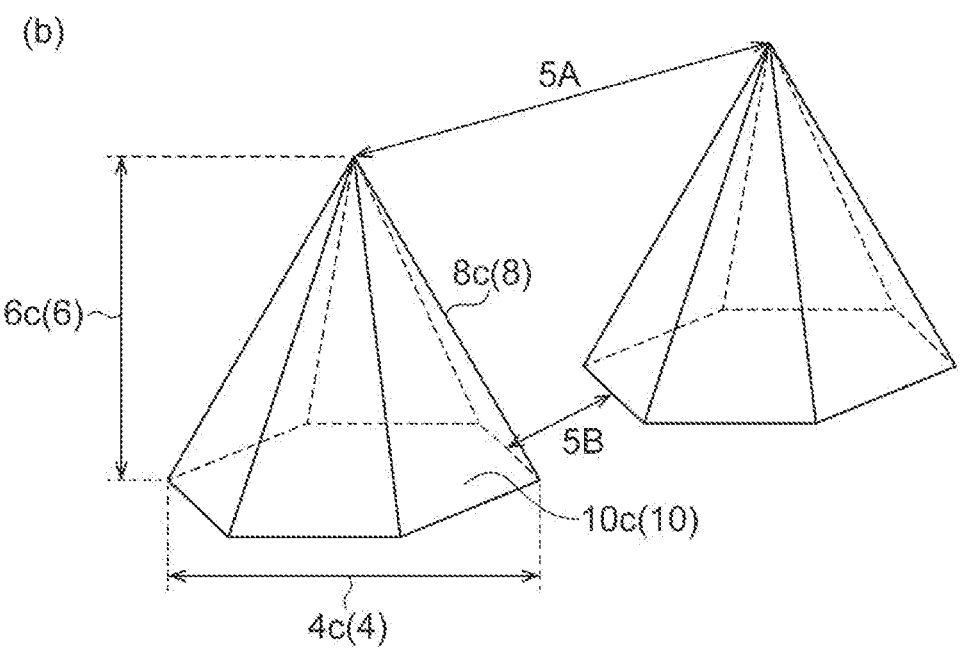

Fig.6
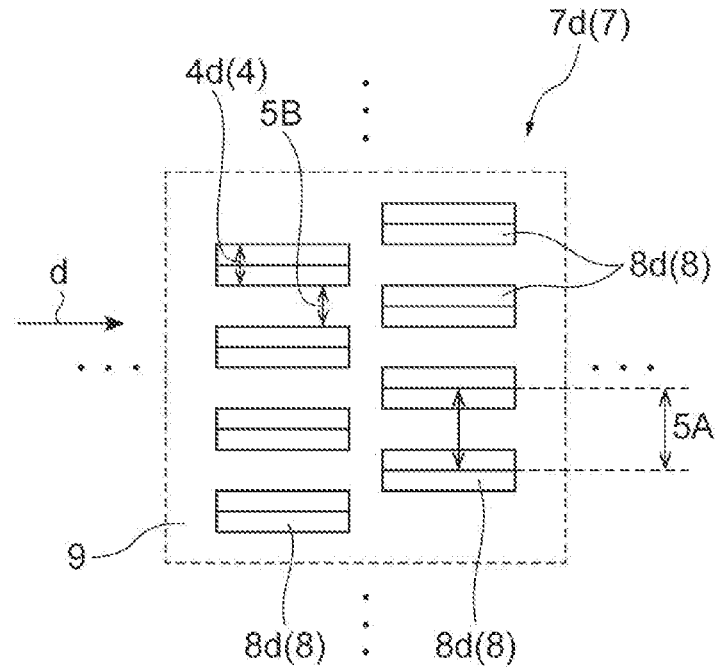
(a)
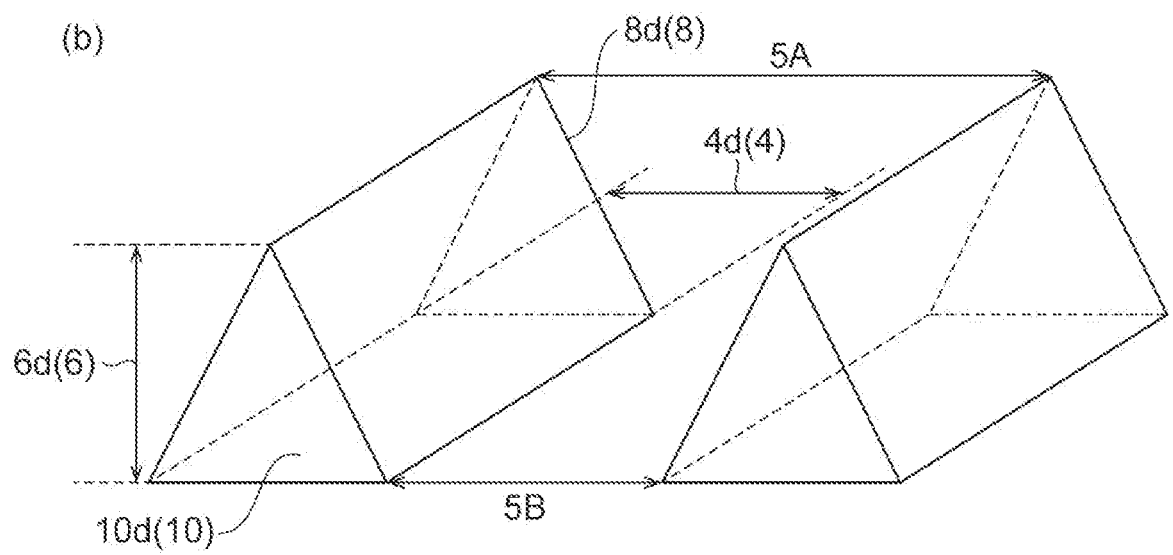
(b)

MEMBRANE CARRIER, KIT FOR TESTING LIQUID SAMPLE USING SAME, AND MANUFACTURING METHOD THEREOF

CROSS-REFERENCE TO RELATED APPLICATIONS

This application is a U.S. National Stage Application filed under 35 U.S.C. § 371 of International Application No. PCT/JP2018/012926, filed Mar. 28, 2018, which claims the benefit of Japanese Application No. JP 2017-062948, filed Mar. 28, 2017. Both of these applications are hereby incorporated by reference in their entireties.

TECHNICAL FIELD

The present invention relates to a membrane carrier, a liquid sample test kit using the carrier and a method for producing the test kit.

BACKGROUND ART

Recently, Point of Care Testing (POCT) reagents using, for example, antigen-antibody reactions for determining contraction of infectious diseases, pregnancy, blood sugar level and the like, have attracted attention. The POCT reagents, which are test reagents used near subjects or directly used by the subjects, have such characteristics as capability of determination of test results in a short time, simple operation and low cost. By virtue of these characteristics, the POCT reagents are frequently used in, for example, medical examinations at the stage of mild symptoms and regular medical examinations and used as an important examination tool in home medical care which is expected to expand from now on.

In most POCT reagents, determination is made by introducing a liquid sample such as blood in a test kit and detecting a predetermined target substance contained in the liquid sample. As a method for detecting a predetermined target substance from a liquid sample, immunochromatography is frequently used. The immunochromatography is a technique for detecting a target substance by adding a liquid drop onto a membrane carrier of a test kit, allowing the liquid drop to move on the membrane carrier, allowing a target substance to bind to marker particles (hereinafter also simply referred to as the particle) bound to an antibody or an antigen specifically reacting with the target substance and suspended or dissolved in a liquid sample, and allowing these particles to further bind specifically to a substance (hereinafter referred to as a detection substance) immobilized in the test kit to produce a color or weight change, and detecting the change. The detection substance may be called also as a reagent.

As a technique for detecting a target substance, a technique for detecting a color change produced by using marker particles is well known. Examples of the marker particles include colored latex particles, fluorescent latex particles and metallic colloidal particles.

In the detection method using marker particles as mentioned above, it is known that as the size of the marker particles increases, the sensitivity is improved. Patent Literatures 1 to 2 show that, in immunodiagnosis using turbidimetry, if the latex diameter increases, light scattering intensity increases and sensitivity increases.

As the POCT reagent for optically determining a color change, lateral flow type kit using a nitrocellulose membrane is often used. The nitrocellulose membrane has many micropores and a liquid sample moves through the micropores with the help of capillary force. In contrast, the pores of nitrocellulose membrane are as fine as the order of several µm. Because of this, there was an upper limit to the diameter of marker particles.

Further, the nitrocellulose membrane, which is derived from a natural product, has pores non-uniform in size. Because of this, the diameter of marker particles to be developed was set to be smaller so as not to produce problems such as clogging; whereas, the sensitivity was low.

Patent Literatures 1 to 4 show that the measurable range of concentration in turbidimetry can be extended by using two types or more latex particles different in diameter in combination.

However, in the immunochromatography, since a nitrocellulose membrane carrier having micropores was used, the size of a marker particle is limited. The effect of the combination use of two types or more latex particles different in diameter on performance was still unknown.

Patent Literature 5 discloses a liquid sample test kit having a microstructure formed therein in place of using a nitrocellulose membrane carrier; however, the effect of a latex diameter on the performance is not disclosed.

CITATION LIST

Patent Literature

Patent Literature 1: Japanese Examined Patent Publication No. S63-14783
Patent Literature 2: Japanese Patent No. 2588174
Patent Literature 3: Japanese Patent No. 3513075
Patent Literature 4: Japanese Unexamined Patent Publication No. H10-123137
Patent Literature 5: WO 2016/098740

SUMMARY OF INVENTION

Technical Problem

The present invention was made in view of the aforementioned problems and is directed to provide a membrane carrier enabling highly sensitive detection.

Solution to Problem

More specifically, the present invention is as follows.
(1) A membrane carrier comprising a flow path, wherein a microstructure is formed at a bottom of the flow path, and a particle to which an antibody or an antigen binds is arranged in at least a part on the flow path, the particle having a diameter of 500 nm or more and 100 µm or less.
(2) The membrane carrier according to (1), wherein an average horizontal distance between adjacent microstructures is at least 3 times the diameter of the particle and 300 µm or less.
(3) The membrane carrier according to (1) or (2), wherein the particle is one or more selected from the group consisting of a colored latex particle and a fluorescent latex particle.
(4) The membrane carrier according to any one of (1) to (3), wherein the membrane carrier is a membrane carrier for a test kit of detecting a target substance in a liquid sample, and the antibody and antigen specifically react with a target substance in the liquid sample.

(5) The membrane carrier according to (4), comprising a detection zone for detecting the target substance in the liquid sample.

(6) The membrane carrier according to (5), wherein the detection zone produces a color change when the target substance is detected.

(7) A method for manufacturing a liquid sample test kit, comprising immobilizing a detection substance producing a color change by holding a target substance in the detection zone of the membrane carrier according to (6).

(8) A liquid sample test kit comprising the membrane carrier according to any one of (1) to (6).

Advantageous Effects of Invention

According to the membrane carrier of the present invention, a highly sensitive test can be carried out.

BRIEF DESCRIPTION OF DRAWINGS

FIG. 3 shows (a) a plan view (top view) of microstructures which is an embodiment of the present invention; and (b) a perspective view of a convex portion constituting the microstructure shown in (a).

FIG. 4 shows (a) a plan view (top view) of a microstructure which is an embodiment of the present invention; and (b) a perspective view of a convex portion constituting the microstructure shown in (a).

FIG. 5 shows (a) a plan view (top view) of a microstructure which is an embodiment of the present invention; and (b) a perspective view of a convex portion constituting the microstructure shown in (a).

FIG. 6 shows (a) a plan view (top view) of a microstructure which is an embodiment of the present invention; and (b) a perspective view of a convex portion constituting the microstructure shown in (a).

DESCRIPTION OF EMBODIMENTS

Embodiments of the present invention will be described below.

A membrane carrier according to an embodiment is a membrane carrier for a liquid sample test kit, which detects a target substance in a liquid sample.

Herein, the target substance, which is not limited, may be any substance as long as it can undergo an antigen-antibody reaction with various pathogens, various clinical markers, antibodies or antigens. Examples of the target substance include, but are not particularly limited to, antigens of viruses such as influenza virus, norovirus, adenovirus, RS virus, HAV, HBs and HIV; antigens of bacteria such as MRSA, Group-A *Streptococcus*, Group-B *Streptococcus* and *Legionella* bacteria; toxins produced by bacteria, *Mycoplasma, Chlamydia trachomatis*, hormones such as human chorionic gonadotropin; and C reactive protein, myoglobin, myocardial troponin, various tumor markers, agrochemicals, environmental hormones, *Treponema pallidum* (TP) antibodies (TPAb) and pylori antibodies. If the target substance is particularly an item that must be quickly detected and treated, such as influenza virus, norovirus, C reactive protein, myoglobin and myocardial troponin, the liquid sample test kit and membrane carrier according to the embodiment are extremely useful. The target substance may be an antigen, which solely induces an immune response, or may be a hapten, which cannot induce an immune response by itself but can induce an immune response if it binds to an antibody through an antigen-antibody reaction. The target substance is usually suspended or dissolved in a liquid sample. The liquid sample may be a sample obtained by suspending or dissolving the target substance in, for example, a buffer solution.

Figure 1:
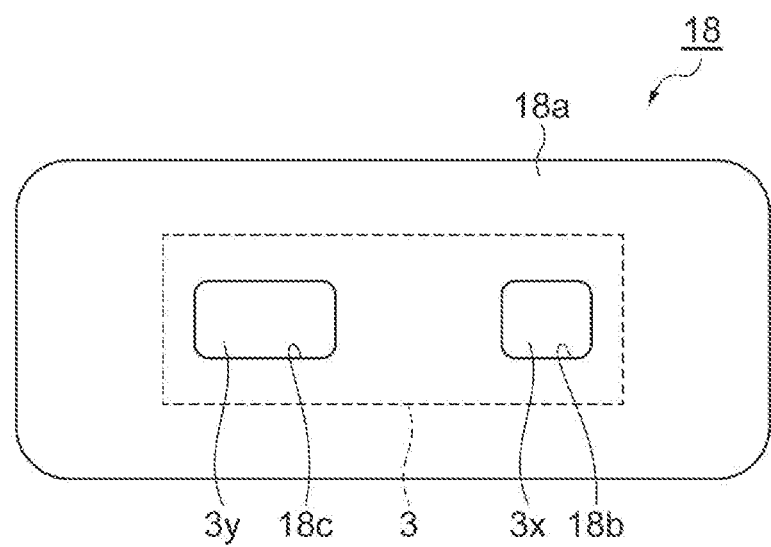
FIG. 1 shows a schematic top view of a test kit which is an embodiment of the present invention.

The liquid sample test kit according to the embodiment (hereinafter referred to also simply as the "test kit") detects a target substance in a liquid sample. FIG. 1 is a schematic top view of a test kit. For example, as shown in FIG. 1, a test kit 18 has a membrane carrier 3 and a case 18a for accommodating the membrane carrier 3. The membrane carrier 3 has, in the surface thereof, a drop zone 3x on which a drop of a liquid sample is delivered and a detection zone 3y for detecting a target substance in a liquid sample. The drop zone 3x is exposed in a first opening 18b of the case 18a. The detection zone 3y exposed in the second opening 18c of the case 18a.

Figure 2:
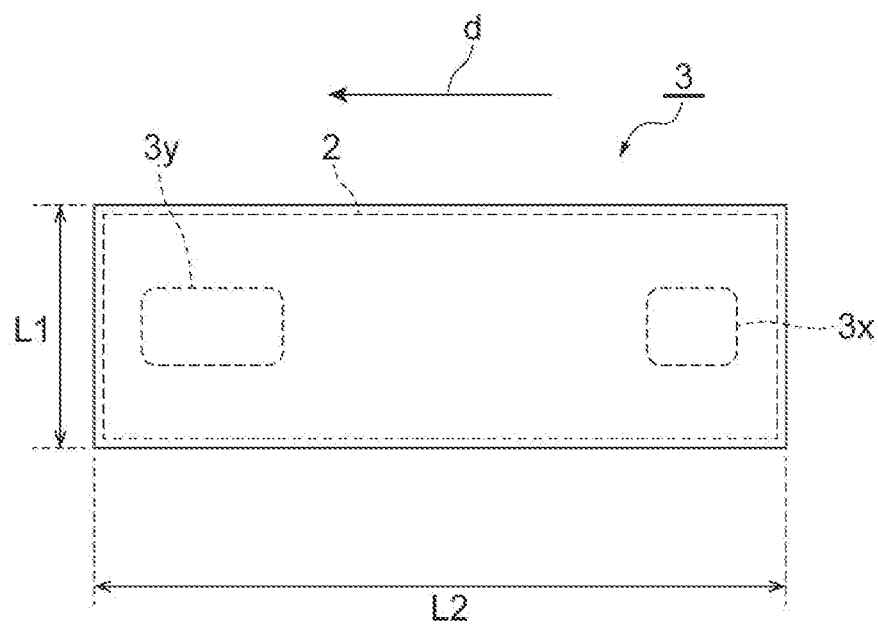
FIG. 2 shows a schematic top view of a membrane carrier which is an embodiment of the present invention.

FIG. 2 is a schematic top view of the membrane carrier 3. As shown in FIG. 2, the membrane carrier 3 has at least one flow path 2 for transporting a liquid sample and a label (not shown, details will be described later) provided on the membrane carrier so as to successfully react with a target substance. The label is constituted of the particle and an antibody or an antigen bound to the particle. The antibody and antigen may be an antibody and an antigen, each of which specifically reacts with a target substance in a liquid sample. The label may be provided in at least a part on the flow path 2 of the membrane carrier 3. At the bottom of the flow path 2, a microstructure is provided (not shown, details will be described later). The microstructure is present at least between the drop zone 3x and the detection zone 3y. The microstructure may be provided over the entire surface of the membrane carrier 3. The entire surface of the membrane carrier 3 may serve as the flow path 2 for a liquid sample. Owing to the microstructure, capillary action is produced. A liquid sample is transported from the drop zone 3x to the detection zone 3y (along transport direction d) through the microstructure with the help of the capillary action produced by the microstructure. During the process of transporting, a target substance in a liquid sample is bound to a label. When the target substance to which the label bound is detected in the detection zone 3y, the color of the detection zone 3y changes.

The entire shape of the membrane carrier 3 is not particularly limited; however, the shape may be, for example, a polygon such as a rectangle, a circle or an ellipsoid. If the membrane carrier 3 is a rectangle, the length (length of the shorter side) L1 of the membrane carrier 3 may be, for example, 2 mm or more and 100 mm or less and the width (length of the longer side) L2 of the membrane carrier 3 may be, for example, 2 mm or more and 100 mm or less. The thickness of the membrane carrier excluding the heights of the microstructure, may be, for example, 0.1 mm or more and 10 mm or less.

FIGS. 3 to 6 and 8 each show a microstructure provided at the bottom of the flow path according to the embodiment and an example of convex portions constituting the microstructure. In each of FIGS. 3 to 6, (a) is a plan view (top view) of microstructure; and (b) is a perspective view of one of the convex portions constituting the microstructure. As shown in FIGS. 3 to 6 and 8, a microstructure 7 is an assembly of convex portions 8. More specifically, the membrane carrier 3 has a flat part 9 corresponding to the bottom of the flow path 2 of a liquid sample and a plurality of convex portions 8 corresponding to the flat part 9. The space between the convex portions 8 serves as flow path 2 for transporting a liquid sample along the surface of the membrane carrier 3 with the help of capillary action. In other words, space in the microstructure 7 serves as the flow path 2 for transporting a liquid sample along the surface of the membrane carrier 3 by capillary action. The convex portions 8 may be arranged on the surface of the membrane carrier 3 in a regular manner or a translational symmetric manner.

Figure 8:
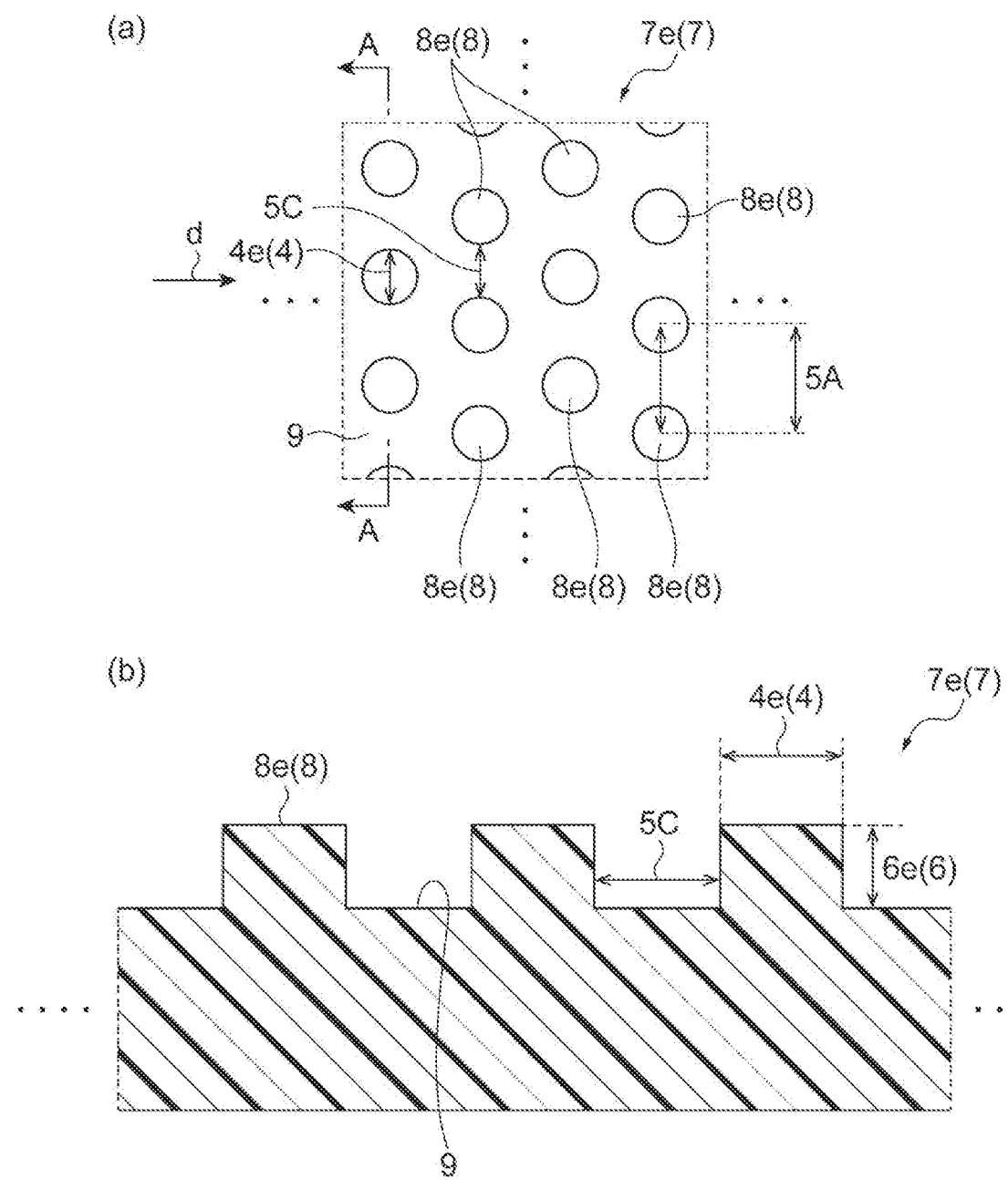
FIG. 8 shows (a) a top view of microstructures according to an embodiment of the present invention; and shows (b) a sectional view of a membrane carrier having the microstructures shown in (a).

The shape of convex portions 8 constituting the microstructure 7 can be freely selected. Examples of the shape of the convex portions 8 include a cone, a polygonal pyramid, a truncated cone, a truncated polygonal pyramid, a cylinder, a polygonal column, a hemisphere and a semi-ellipsoid. For example, the shape of the convex portions 8a may be a cone as shown in FIG. 3. For example, the shape of the convex portions 8b may be a square pyramid as shown in FIG. 4. For example, the shape of the convex portions 8c may be a hexagonal pyramid as shown in FIG. 5. For example, the shape of the convex portions 8d may be a horizontally-long triangular prism (triangular prism placed such that a side surface of the triangular prism (a rectangular surface) is in contact with the flat part 9) as shown in FIG. 6. For example, the shape of the convex portions 8e may be a cylinder, as shown in FIG. 8. For the reasons that when the microstructure 7 is looked down (seen from the top) the entire surface of the membrane carrier 3 can be seen and a color change when a target substance is detected can be easily checked by an optical means, a cone structure such as a cone and polygonal pyramid is suitable as the shape of the convex portions 8, among the aforementioned shapes.

The shape of the convex portions 8 constituting the microstructure 7 is not necessary to be a geometrically accurate shape and may be a shape having a round corner and a shape having micro-convexoconcaves in the surface.

The diameter 4 of each of the bottom surfaces 10 of the convex portions 8 constituting the microstructure 7 may be 10 µm or more and 1000 µm or less and more preferably 15 µm or more and 1000 µm or less. The diameter 4 of the bottom surface 10 of the convex portion 8 may vary (be different from each other) among a plurality of convex portions 8 within the above range. If the diameter 4 of each of the bottom surfaces 10 of the convex portions 8 is 10 µm or more, the microfabrication cost of a mold for forming the microstructure 7 decreases and an infinite number of microstructure 7 can be easily and uniformly formed on the surface of the large-area membrane carrier 3. Accordingly, a microstructure constituted of the convex portions 8 having the bottom surface 10 of 10 µm or more in diameter 4, is more practical. If the diameter of each of the bottom surfaces 10 of the convex portions 8 is 10 µm or more, capillary force required for moving a liquid sample tends to increase. If the diameter 4 of each of the bottom surfaces 10 of the convex portions 8 is 1000 µm or less, the volume of metal scraped out from a metal member at the time of forming a mold can be reduced, with the result that fabrication costs for the mold and the membrane carrier 3 can be suppressed. If the diameter of each of the bottom surfaces 10 of the convex portions 8 is 1000 µm or less, the area of flow path 2 in the membrane carrier 3 can be reduced, with the result that a liquid sample test kit 18 can be miniaturized. This is advantageous for shipping the liquid sample test kit 18 itself.

The diameter 4 of each of the bottom surfaces 10 of the convex portions 8 is defined as the representative length of the bottom surface 10 of the convex portion 8. The representative length defining the bottom surface 10 is a diameter if the shape of the bottom surface 10 is a circle; the length of the shortest side if the shape is a triangle or a rectangle; the length of the longest diagonal line if the shape is a polygon of a pentagon or more; and a maximum length of the bottom surface 10 in the case of shapes except the aforementioned ones.

Figure 7:
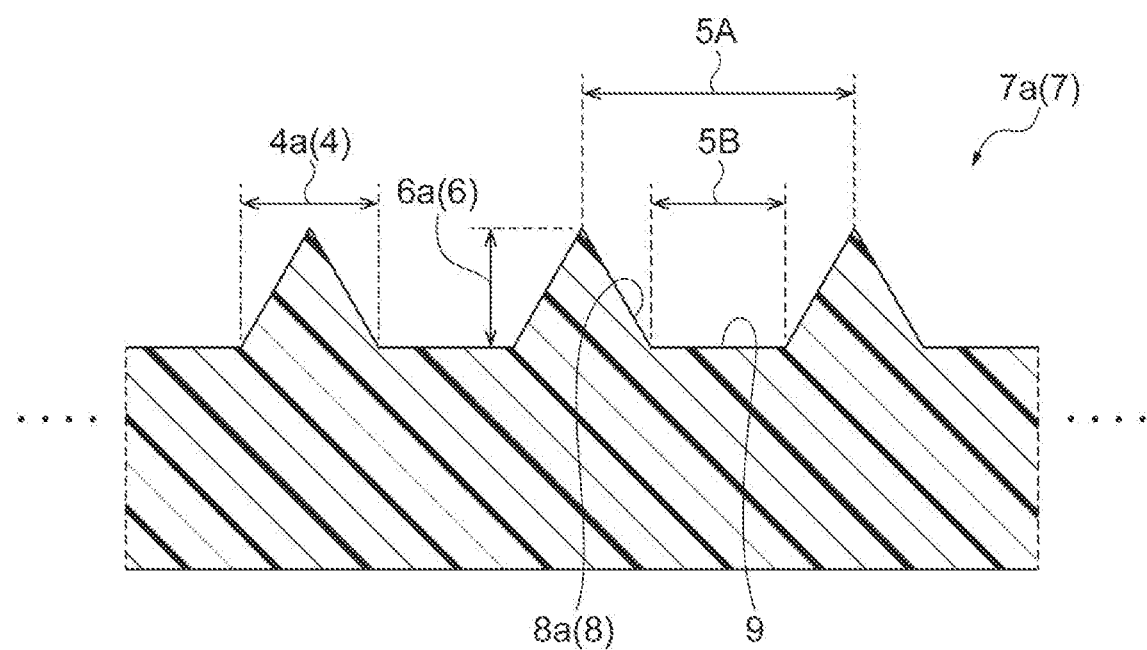
FIG. 7 shows a sectional view of a membrane carrier having a microstructure which is an embodiment of the present invention.

FIG. 7 is an aligned sectional view of the membrane carrier having a microstructure 7a taken along the line VII-VII shown in FIG. 3. As shown in FIG. 3 and FIG. 7, if the shape of the convex portion 8a is a cone, the diameter 4a of the bottom surface 10a of the convex portion 8a corresponds to the diameter of the bottom (circle) of the cone. As shown in FIG. 4, if the shape of the convex portion 8b is a regular square pyramid, the diameter 4b of the bottom surface 10b of the convex portion 8b is the length of sides of the bottom surface (regular square) 10b. As shown in FIG. 5, if the shape of the convex portion 8c is a regular hexagonal pyramid, the diameter 4c of the bottom surface 10c of the convex portion 8c is the length of a diagonal line (length of the longest diagonal line) passing through the center of the bottom surface (regular hexagon) 10c. As shown in FIG. 6, if the shape of the convex portion 8d is a horizontally-long triangular prism, the diameter 4d of the bottom surface 10d of the convex portion 8d is the length of the shortest side of the bottom surface (rectangle) 10d (in FIG. 6, the length of the side perpendicular to the transport direction d of a liquid sample). FIG. 8(b) is an aligned sectional view of the membrane carrier having a microstructure 7e taking along the line A-A shown in FIG. 8(a). As shown in FIG. 8, if the shape of convex portions 8e is a cylinder, the diameter 4e of the bottom of the convex portion 8e is the diameter of circular bottom of the cylinder.

The height 6 of each of the convex portions 8 constituting the microstructure 7 is preferably 10 µm or more and 500 µm or less and more preferably 15 µm or more and 500 µm. The height 6 of the convex portions 8 may vary (be different from each other) among a plurality of convex portions 8 within the above range. If the height 6 of the convex portions 8 is 10 µm or more, the volume of the flow path 2 increases, with the result that a liquid sample can be developed in a shorter time. If the height 6 of each of the convex portions 8 is 500 µm or less, time and cost for forming the microstructure 7 can be reduced, with the result that it becomes easy to prepare the microstructure 7.

The height 6 of the convex portion 8 is defined as a maximum length of the convex portion 8 in the direction perpendicular to the flat part 9. As shown in FIG. 3 and FIG. 7, if the shape of the convex portion 8a is a cone, the height 6a of the convex portion 8a is a maximum length of the convex portion 8a in the direction perpendicular to the flat part 9 (the height of the cone). As shown in FIG. 4, if the shape of the convex portion 8b is a square pyramid, the height 6b of the convex portion 8b is a maximum length of the convex portion 8b in the direction perpendicular to the flat part 9 (the height of the square pyramid). As shown in FIG. 5, if the shape of the convex portion 8c is a hexagonal pyramid, the height 6c of the convex portion 8c is a maximum length of the convex portion 8c in the direction perpendicular to the flat part 9 (the height of the hexagonal pyramid). As shown in FIG. 6, if the shape of the convex portion 8*d* is a horizontally-long triangular prism, the height 6*d* of the convex portion 8*d* is a maximum length of the convex portion 8*d* in the direction perpendicular to the flat part 9 (the height of the horizontally-long triangular prism). As shown in FIG. 8, if the convex portion 8*e* is a cylinder, the height 6*e* of the convex portion 8*e* is the maximum length of the convex portion 8*e* in the direction perpendicular to the flat part 9 (the height of the cylinder).

The average horizontal distance between adjacent microstructures, in the case where the horizontal distance between adjacent microstructures (for example, between convex portions 8) varies depending on the height of the convex portions 8, like a cone, a hemisphere and a semi-ellipsoid, is specified as an average value of the farthest horizontal distance 5A between adjacent microstructures (nearest center-to-center distance) and the nearest horizontal distance 5B between the adjacent microstructures, i.e., (5A+5B)/2, as shown in FIGS. 3 to 7.

The average horizontal distance between adjacent microstructures, in the case where the horizontal distance between adjacent microstructures does not vary depending of the height of the microstructure, like a column, is specified as the distance of the space 5C between microstructures (convex portions 8) as shown in the distance 5C of the space between adjacent microstructures in FIG. 8 (convex portions 8 are cylinders).

The average horizontal distance between adjacent microstructures may be at least 3 times or at least 4 times and at most 600 times or at most 500 times the diameter of the particle. If the average horizontal distance between adjacent microstructures is at least 3 times the diameter of the particle, the risk that the liquid sample flow is disrupted by resistance of the particle, with the result that the membrane carrier may not be used as a kit, is more suppressed.

The average horizontal distance between adjacent microstructures may be 1.5 μm or more, 2.0 μm or more or 2.5 μm or more and may be 300 μm or less, 250 μm or less or 200 μm or less. If the average horizontal distance between adjacent microstructures is 300 μm or less, the risk that the area at which a liquid sample is in contact with the flow path reduces and a reduction of capillary force is suppressed, with the result that the liquid sample cannot be moved, is suppressed.

The average horizontal distance between adjacent microstructures is preferably at least 3 times the diameter of the particle and 300 μm or less, and more preferably, at least 4 times the diameter of the particle and 300 μm or less.

The microstructure 7 and the membrane carrier 3 of the liquid sample test kit 18 of the embodiment may be made of a thermoplastic. In other words, the membrane carrier 3 having the microstructure 7 can be produced by processing a film-like base material made of a thermoplastic. Examples of the processing method include thermal imprint, UV imprint, injection molding, etching, photolithography, machine cutting and laser processing. Of them, thermal imprint to a thermoplastic is suitable as a method for applying a precise processing at low cost. Examples of the thermoplastic include a polyester resin, a polyolefin resin, a polystyrene resin, a polycarbonate resin, a fluororesin and an acrylic resin. More specifically, various types of resins including polyethylene terephthalate (PET), a cycloolefin polymer (COP), polypropylene (PP), polystyrene (PS), polycarbonate (PC), polyvinylidene fluoride (PVDF) and polymethylmethacrylate (PMMA), can be used.

In the case of processing using a mold, such as imprint and injection molding, since the top of a cone is narrow compared to the bottom, the volume of metal scraped out in forming the mold is smaller than a columnar mold having the same bottom area, and thus, the mold can be prepared at low cost with a cone. In this case, a target substance in a liquid sample can be detected at low cost.

The label is constituted of the particle and an antibody or an antigen bound to the particle. The label can bind to a target substance via the antibody or antigen.

The label may be provided to at least a part of the flow path at the upstream side of the detection zone 3*y* (between the drop zone 3*x* and detection zone 3*y* (including drop zone 3*x*)). The label may be provided to at least a part of the drop zone 3*x* or over the whole drop zone 3*x*. Alternatively, the label may be provided together with a member to be used in the test kit 18 to the flow path 2. The label reacted with (bound to) a target substance is held by a detection substance (through reaction (binding) of the detection substance with the target substance) in the detection zone 3*y*. In this manner, a color change (color produced by a label) is produced in the detection zone 3*y*.

The antibody or antigen may be a binding fragment. The binding fragment refers to a fragment that can specifically bind to a target substance; for example, an antigen binding fragment of an antibody or an antibody binding fragment of an antigen is referred to.

Examples of the particle include colloidal particles and latex particles. The particles may have magnetic property or fluorogenicity. Examples of the colloidal particles include metallic colloidal particles such as gold colloidal particles and platinum colloidal particles. The particles are preferably latex particles in view of control of particle size, dispersion stability and binding ability. The material for latex particles is not particularly limited; however, polystyrene is preferable.

In view of visibility, the particles are preferably colored particles or fluorescent particles and more preferably colored particles. The colored particles are satisfactory if the color thereof is detectable by the naked eye. The fluorescent particles are satisfactory if they contain a fluorescence substance. The particles may be colored latex particles or fluorescent latex particles. If the particles are colored latex particles, the color change mentioned above is suitably detected visually. If the particles are fluorescent latex particles, the color change mentioned above is suitably detected by fluorescence-intensity measurement.

The diameter of the particle is 500 nm or more and 100 μm or less. The diameter of the particle may be, 600 nm or more, 800 nm or more, 1 μm or more, 1.2 μm or more, 1.5 μm or more, 2 μm or more or 2.5 μm or more and 80 μm or less, 60 μm or less, 50 μm or less, 20 μm or less, 10 μm or less or 5 μm or less. The diameter of the particle is preferably 600 nm or more and 80 μm or less, 800 nm or more and 60 μm or less, 1 μm or more and 50 μm or less, 1.2 μm or more and 20 μm or less or 2 μm or more and 10 μm or less. If it is less than 500 nm, the color change produced when the particle is immobilized in the detection zone 3*y* is small and detection sensitivity can be reduced. If the diameter is larger than 100 μm, liquid sample flow is disrupted by resistance of the particles, with the result that the membrane carrier cannot be used as a kit.

The particle diameter refers to a diameter of a particle measured by dynamic light scattering. The dynamic light scattering is described, for example, in Japanese Patent No. 5147011 and home page of Beckman Coulter, Inc. ("measurement principle of dynamic light scattering", <URL: https://beckman.jp/column/particle/m principle/>).

In order to realize a highly sensitive test, it is preferable to use particles different in diameter in combination. According to the present inventors, the reason is presumably as follows. Since the contact area between a detection substance and a microstructure varies depending on the particle diameter, the time required for an antigen-antibody reaction varies. The reaction time is affected by the flow rate of a liquid sample, and the flow rate changes depending on the height in the flow path from the bottom. Since the flow rate at which a reaction with a detection substance easily proceeds varies depending on the particle diameter, the height, at which adhesion to a microstructure can be easily made, varies. As a result, if a plurality of types of particles are developed in a microstructure, the particles are separated into those which easily adhere to the upper portion of the structure and those which easily adhere to the lower portion of the structure. Because of this, the total adhesion area increases compared to the case where a single type of particle alone is developed. As a result, a target substance can be easily detected and sensitivity is improved.

It is preferable that a plurality of types of particles different in diameter are used; and more preferable that two types of particles different in particle diameter are used. In the case where two types of particles different in particle diameter are used, provided that particles having a smaller diameter is represented by P1 and the particle having a larger diameter is represented by P2, the mass ratio (P1/P2) is preferably 10/90 to 90/10, more preferably 30/70 to 70/30 and further preferably 50/50.

As described above, the membrane carrier 3 has microstructures 7 formed over one of the surfaces of the membrane carrier 3, the flow path 2 formed of the microstructures 7 and used for transporting a liquid sample and a label provided on the membrane carrier 3 so as to successfully react with a target substance and having the particle and an antibody or antigen bound to the particle. The diameter of the particle is 500 nm or more and 100 µm or less. The membrane carrier 3 may be a membrane carrier 3 for the liquid sample test kit 18 for detecting a target substance in a liquid sample.

In the liquid sample test kit 18 according to the embodiment, the detection zone 3y of the membrane carrier 3 produces a color change when a target substance is detected. The color change may be a color change observable by an optical means.

As the optical means, two methods: a visual determination means and means of measuring a fluorescence intensity, are mostly mentioned. In the case of visual determination, it is preferable to produce a color change expressed by a color difference (ΔE described in JIS Z8781-4:2013) of 0.5 or more between two color stimuli before and after detection when the color is measured by the color system of CIE1976L*a*b* color space. If the color difference is 0.5 or more, visually determination of color difference can be easily made. In the case of determination based on fluorescence-intensity measurement, it is preferable to produce a color difference satisfying a ratio of the fluorescence intensity (F11) in the detection zone 3y to the fluorescence intensity (F12) in upstream region and downstream region adjacent to the detection zone 3y, (F11/F12)=10/1 or more. If the ratio is 10/1 or more, signal and noise can be easily separated.

To prepare the detection zone 3y in the liquid sample test kit 18 of the embodiment, a detection substance is immobilized in at least part of the flow path 2, in an embodiment. More specifically, a detection substance detecting a target substance is immobilized in the detection zone 3y. A color change in the detection zone 3y is produced by holding a target substance by the detection substance (through reaction with the detection substance) in the detection zone 3y.

In other words, a method for producing the liquid sample test kit 18 comprises a step of immobilizing, to the detection zone 3y, a detection substance which produces a color change by holding the target substance in the detection zone 3y. For the reason that a detection substance (reagent) can be efficiently immobilized in the detection zone 3y, the surface treatment may be previously applied to the site of the membrane carrier 3, at which the detection zone 3y is to be provided.

The surface treatment method is not limited and, for example, various methods such as UV irradiation, a UV/ozone treatment, various plasma treatments and surface modification with, for example, 3-aminopropyltriethoxysilane or glutaraldehyde, can be used.

In the embodiment, as the detection substance (reagent), for example, an antibody is mentioned. The antibody is an antibody which binds to a target substance through an antigen-antibody reaction, and may be a polyclonal antibody or a monoclonal antibody.

The color change in the detection zone 3y may be produced by a label having a particle and an antibody or an antigen bound to the particle. The color change is produced by, for example, holding a label by a detection substance (through a reaction with (binding to) the detection substance) in the detection zone 3y and producing a color.

A method for testing a liquid sample according to one aspect of the embodiment is a test method using the test kit 18.

The method for testing a liquid sample using the test kit 18 may comprise a step of preparing a mixed liquid sample by mixing the liquid sample and a label specifically binding to a target substance in the liquid sample to mutually bind the target substance and the label; a step of delivering a drop of the mixed liquid sample to the drop zone 3x provided in the membrane carrier 3; a step of transporting the mixed liquid sample from the drop zone 3x to the detection zone 3y through the microstructure 7; and a step of detecting a color change (color of label) in the detection zone 3y.

Alternatively, the above test method may comprise a step of delivering a drop of a liquid sample to the drop zone 3x in the surface of the membrane carrier 3; a step of transporting the liquid sample from the drop zone 3x to the detection zone 3y through the microstructure 7 with the help of capillary action exerted by the microstructure 7 (convex portions 8) formed on the surface of the membrane carrier 3; and a step of binding a target substance in a liquid sample to the label via the antibody or the antigen, further, binding the target substance to a reagent immobilized in the detection zone 3y and detecting a color change in the detection zone 3y (optically determining the presence or absence of color change).

In the step of mutually binding a target substance and a label in the above test method, a method for mixing a liquid sample and the label is not particularly limited. For example, a method of adding a liquid sample in a container containing the label or a method of mixing a liquid containing, for example, a label, and a liquid sample may be employed. Alternatively, a filter is inserted in a drip opening of a container containing, for example, a liquid sample, and a label may be immobilized in the filter.

EXAMPLES

The embodiments will be described; however, the embodiments are not limited by these Experimental Examples.

Experimental Example 1

<Preparation of Mold>

The mold was prepared by laser processing and machine cutting. The mold is made of aluminum alloy A5052. In the center of the mold, conical concave portions having a diameter of 25 μm and a depth of 30 μm are provided at the nearest center-to-center distance (the farthest horizontal distance) of 30 μm, the nearest horizontal distance (the nearest horizontal distance) between adjacent microstructures of 5 μm and an average distance of 17.5 m, in a staggered arrangement, within the range of 3 cm×3 cm, as shown in FIG. 3.

In order to easily separate the mold and a thermoplastic without fail at the time of transfer printing, a release treatment was applied to the convex-concave surface of the mold. The release treatment was carried out by soaking the mold in Optool HD-2100TH manufactured by Daikin Industries Ltd., for about one minute, drying, and then, allowing the mold to stand still overnight.

<Transfer Printing of Microstructure>

Using the mold obtained as mentioned above, the microstructure was transfer-printed to a thermoplastic. As the thermoplastic, polystyrene (Denka styrene sheet manufactured by Denka Company Limited, film thickness 300 μm) was used. As the processing method, thermal imprint was used. As the apparatus, X-300 manufactured by SCIVAX was used. Transfer printing was carried out at a molding temperature of 120° C. and an applied pressure of 5.5 MPa for 10 minutes. After the transfer-printing, the thermoplastic and the mold were cooled up to 80° C. while applying the pressure, and then, the pressure was eliminated to prepare a membrane carrier.

In the membrane carrier manufactured, the farthest horizontal distance, nearest horizontal distance, average distance, and diameter and height of the convex portions are shown in Table 1. The convex portions are cones. The thickness of the membrane carrier except the height of microstructure (convex portions) is 0.2 mm.

<Preparation of Detection Zone>

At the positions of the membrane carrier manufactured above at a distance of 0.6 cm and 1.0 cm from the lower edge, an anti-type A influenza NP antibody suspension solution, and an anti-type B influenza NP antibody suspension solution were applied in a width of 3 cm (coating amounts each were 3 μL), and sufficiently dried by hot air to immobilize the detection substances.

<Preparation of Label>

Purified anti-type A influenza virus NP antibody (another antibody as used in the above) and purified anti-type B influenza virus NP antibody (another antibody as used in the above) were used. The anti-type A influenza virus NP antibody was covalently labeled with red latex particles (SC-042-R polystyrene latex particles, colored latex particles, manufactured by JSR Life Sciences Corporation) having a particle diameter of 0.2 Lm, suspended in a Tris buffer solution containing a sugar, a surfactant and a protein such that the concentration of the latex particles became 0.025 mass/vi %, and ultrasonically treated to prepare an anti-type A label sufficiently dispersed and suspended. Anti-type B label was similarly prepared by labeling an anti-type B influenza virus NP antibody with blue latex particles.

The anti-type A label and the anti-type B label were mixed and applied to the glass fiber having a size of 3 cm×1 cm (33GLASS No. 10539766, manufactured by Schleicher & Schuell) in an amount of 50 μL per square centimeter and dried well by hot air to produce a label pad. Thereafter, the label pad was overlapped with the edge portion (just by 2 mm) of the membrane carrier prepared and cut into strips having a width of 5 mm by a cutter to prepare integrated liquid sample test kits.

<Detection Evaluation>

On the edge of the liquid sample test kit prepared as mentioned above, the liquid sample (100 μL) was dropped. The liquid sample was diluted with a specimen suspension solution attached to Quick navi-Flu manufactured by Denka Seiken Co., Ltd., as a dilution solution. A maximum dilution rate (maximum visible-determination allowable dilution rate of type A), at which the presence or absence of a colored line cannot be visually observed 10 minutes after initiation of the test, was obtained by increasing the dilution rate of type A influenza virus A/Beijing/32/92 (H3N2) from $2\times10^4$. A test was carried out at a ½ dilution rate as low as the maximum dilution rate to obtain the time until concentration of the colored line is stabilized (time until the concentration of type A is stabilized) from initiation of the test, as detection time. The results are shown in Tables 1 and 2.

To an edge of the liquid sample test kit manufactured as described above, a liquid sample (100 μL) was added dropwise. The liquid sample was diluted with a specimen suspension solution attached to Quick navi-Flu manufactured by Denka Seiken Co., Ltd., as a dilution solution. A maximum dilution rate (maximum visible-determination allowable dilution rate of type B), at which the presence or absence of a colored line cannot be visually observed 10 minutes after initiation of the test, was obtained by increasing the dilution rate of type B influenza virus B/Shangdong/7/97 from $2\times10^3$. A test was carried out at a ½ dilution rate as low as the maximum dilution rate to obtain the time until concentration of the colored line is stabilized (time until the concentration of type B is stabilized) from initiation of the test, as detection time. The results are shown in Table 1.

The detection time in Table 1 refers to an average value of the time until the concentration of type A is stabilized and the time until the concentration of type B is stabilized.

Overall evaluations were carried out based on the visible-determination allowable dilution rates in accordance with the following criteria and the results are shown in Table 1.

A: Visible-determination allowable dilution rate is $7\times10^3$ or more and detection time is 7 minutes or less.

B: None of A, C and D is applied

C: Visible-determination allowable dilution rate is more than $3\times10^3$ and $4\times10^3$ or less, or detection time is 10 minutes or more.

D: Visible-determination allowable dilution rate is $3\times10^3$ or less.

Experimental Example 2

Experiment was carried out in the same conditions as in Experimental Example 1 except that the latex particle diameter used in the microstructure of Experimental Example 1 was specified as 200 μm. In the membrane carrier manufactured, the convex portions were in the shape of a cone.

The farthest horizontal distance, nearest horizontal distance, average distance and diameter and height of the convex portions are shown in Table.

Experimental Example 3

Experiment was carried out in the same conditions as in Experimental Example 1 except that the latex particle diameter used in the microstructure of Experimental Example 1 was specified as 0.5 µm. In the membrane carrier manufactured, the convex portions were in the shape of a cone. The farthest horizontal distance, nearest horizontal distance, average distance and diameter and height of the convex portions are shown in Table.

Experimental Example 4

Experiment was carried out in the same conditions as in Experimental Example 1 except that the latex particle diameter used in the microstructure of Experimental Example 1 was specified as 1 µm. In the membrane carrier manufactured, the convex portions were in the shape of a cone. The farthest horizontal distance, nearest horizontal distance, average distance and diameter and height of the convex portions are shown in Table.

Experimental Example 5

Experiment was carried out in the same conditions as in Experimental Example 1 except that the latex particle diameter used in the microstructure of Experimental Example 1 was specified as 5 µm. In the membrane carrier manufactured, the convex portions were in the shape of a cone. The farthest horizontal distance, nearest horizontal distance, average distance and diameter and height of the convex portions are shown in Table.

Experimental Example 6

Experiment was carried out in the same conditions as in Experimental Example 1 except that the microstructures of Experimental Example 1 were specified as conical concaves having a diameter of 80 µm, a farthest horizontal distance of 100 µm, a nearest horizontal distance of 20 µm, an average distance of 60 µm and a depth of 100 µm, and that the latex particle diameter was specified as 1 µm. In the membrane carrier manufactured, the convex portions were in the shape of a cone. The farthest horizontal distance, nearest horizontal distance, average distance and diameter and height of the convex portions are shown in Table.

Experimental Example 7

Experiment was carried out in the same conditions as in Experimental Example 1 except that the microstructures of Experimental Example 1 were specified as conical concaves having a diameter of 80 µm, a farthest horizontal distance of 100 µm, a nearest horizontal distance of 20 µm, an average distance of 60 µm and a depth of 100 µm and that the latex particle diameter was specified as 5 µm. In the membrane carrier manufactured, the convex portions were in the shape of a cone. The farthest horizontal distance, nearest horizontal distance, average distance and diameter and height of the convex portions are shown in Table.

Experimental Example 8

Experiment was carried out in the same conditions as in Experimental Example 1 except that the microstructures of Experimental Example 1 were specified as conical concaves having a diameter of 80 µm, a farthest horizontal distance of 100 µm, a nearest horizontal distance of 20 µm, an average distance of 60 µm and a depth of 100 µm, and that the latex particle diameter was specified as 20 µm. In the membrane carrier manufactured, the convex portions were in the shape of a cone. The farthest horizontal distance, nearest horizontal distance, average distance and diameter and height of the convex portions are shown in Table.

Experimental Example 9

Experiment was carried out in the same conditions as in Experimental Example 1 except that the microstructures of Experimental Example 1 were specified as conical concaves having a diameter of 300 µm, a farthest horizontal distance of 450 µm, a nearest horizontal distance of 150 µm, an average distance of 300 µm and a depth of 450 µm, and that the latex particle diameter was specified as 5 µm. In the membrane carrier manufactured, the convex portions were in the shape of a cone. The farthest horizontal distance, nearest horizontal distance, average distance and diameter and height of the convex portions are shown in Table.

Experimental Example 10

Experiment was carried out in the same conditions as in Experimental Example 1 except that the microstructures of Experimental Example 1 were specified as conical concaves having a diameter of 300 µm, a farthest horizontal distance of 450 µm, a nearest horizontal distance of 150 µm, an average distance of 300 µm and a depth of 450 µm, and that the latex particle diameter was specified as 20 µm. In the membrane carrier manufactured, the convex portions were in the shape of a cone. The farthest horizontal distance, nearest horizontal distance, average distance and diameter and height of the convex portions are shown in Table.

Experimental Example 11

Experiment was carried out in the same conditions as in Experimental Example 1 except that the microstructures of Experimental Example 1 were specified as conical concaves having a diameter of 300 µm, a farthest horizontal distance of 450 µm, a nearest horizontal distance of 150 µm, an average distance of 300 µm and a depth of 450 µm, and that the latex particle diameter was specified as 100 µm. In the membrane carrier manufactured, the convex portions were in the shape of a cone. The farthest horizontal distance, nearest horizontal distance, average distance and diameter and height of the convex portions are shown in Table.

Experimental Example 12

Experiment was carried out in the same conditions as in Experimental Example 1 except that, in Experimental Example 1, a 0.025 w/v % suspension solution containing latex particles having a diameter of 0.5 µm and a 0.025 w/v % suspension solution containing latex particles having a diameter of 1 µm were mixed in equal volumes and a label pad was prepared by using the solution. In the membrane carrier manufactured, the convex portions were in the shape of a cone. The farthest horizontal distance, nearest horizontal distance, average distance and diameter and height of the convex portions are shown in Table.

Experimental Example 13

Experiment was carried out in the same conditions as in Experimental Example 1 except that, in Experimental Example 1, a 0.025 w/v % suspension solution containing latex particles having a diameter of 1 μm and a 0.025 w/v % suspension solution containing latex particles having a diameter of 5 μm were mixed in equal volumes and a label pad was prepared by using the solution; and that the microstructures were specified as conical concaves having a diameter of 80 μm, a farthest horizontal distance of 100 μm, a nearest horizontal distance of 20 μm, an average distance of 60 μm and a depth of 100 μm. In the membrane carrier manufactured, the convex portions were in the shape of a cone. The farthest horizontal distance, nearest horizontal distance, average distance and diameter and height of the convex portions are shown in Table.

Experimental Example 14

Experiment was carried out in the same conditions as in Experimental Example 1 except that, in Experimental Example 1, a 0.025 w/v % suspension solution containing latex particles having a diameter of 5 μm and a 0.025 w/v % suspension solution containing latex particles having a diameter of 20 μm were mixed in equal volumes and a label pad was prepared by using the solution; and that the microstructures were specified as conical concaves having a diameter of 300 μm, a farthest horizontal distance of 450 μm, a nearest horizontal distance of 150 μm, an average distance of 300 μm and a depth of 450 μm. In the membrane carrier manufactured, the convex portions were in the shape of a cone. The farthest horizontal distance, nearest horizontal distance, average distance and diameter and height of the convex portions are shown in Table.

Experimental Example 15

Experiment was carried out in the same conditions as in Experimental Example 1 except that the latex particle diameter used in the microstructure of Experimental Example 1 was specified as 0.4 μm. In the membrane carrier manufactured, the convex portions were in the shape of a cone. The farthest horizontal distance, nearest horizontal distance, average distance and diameter and height of the convex portions are shown in Table.

Experimental Examples 16 to 27

Experiments were carried out in the same conditions as in Experimental Examples 3 to 14 except that the particles to be used were changed from colored latex particles to fluorescent latex particles (micromer-F fluorescent latex particles, material: polystyrene manufactured by Corefront Corporation); and that the dilution rate (maximum fluorescence determination allowable dilution rate) at which the presence or absence of a colored line cannot be read by an immunochromato reader (C11787 manufactured by Hamamatsu Photonics K. K.) 10 minutes after initiation of the test was obtained. Except for this was in the same manner as in Experimental Examples 3 to 14. In the membrane carriers manufactured, the farthest horizontal distance, nearest horizontal distance, average distance, diameter of fluorescent latex particles (fluorescent latex particle diameter), and diameter and height of the convex portions are shown in Table 2.

Overall evaluations were carried out based on the fluorescent-determination allowable dilution rates in accordance with the following criteria and the results are shown in Table 2.

A: fluorescence determination allowable dilution rate is $5 \times 10^4$ or more.

B: Overall evaluation of neither A nor C is applied.

C: fluorescence determination allowable dilution rate is $1 \times 10^4$ or more and $2 \times 10^4$ or less.

TABLE 1

| | Experimental Example 1 | Experimental Example 2 | Experimental Example 3 | Experimental Example 4 | Experimental Example 5 | Experimental Example 6 | Experimental Example 7 | Experimental Example 8 |
|---|---|---|---|---|---|---|---|---|
| Farthest horizontal distance (μm) | 30 | 30 | 30 | 30 | 30 | 100 | 100 | 100 |
| Nearest horizontal distance (μm) | 5 | 5 | 5 | 5 | 5 | 20 | 20 | 20 |
| Average distance (μm) | 17.5 | 17.5 | 17.5 | 17.5 | 17.5 | 60 | 60 | 60 |
| Colored latex particle diameter (μm) | 0.2 | 200 | 0.5 | 1 | 5 | 1 | 5 | 20 |
| Diameter of convex portion (μm) | 25 | 25 | 25 | 25 | 25 | 80 | 80 | 80 |
| Height of convex portion (μm) | 30 | 30 | 30 | 30 | 30 | 100 | 100 | 100 |
| Maximum visible-determination allowable dilution rate of type A | $2 \times 10^4$ | Latex was not developed | $4 \times 10^4$ | $5 \times 10^4$ | $6 \times 10^4$ | $5 \times 10^4$ | $6 \times 10^4$ | $7 \times 10^4$ |

TABLE 1-continued

|  | | | | | | | | |
|---|---|---|---|---|---|---|---|---|
| Maximum visible-determination allowable dilution rate of type B | $2 \times 10^3$ | Latex was not developed | $4 \times 10^3$ | $5 \times 10^3$ | $6 \times 10^3$ | $5 \times 10^3$ | $6 \times 10^3$ | $7 \times 10^3$ |
| Detection time | 7 | — | 7 | 7 | 15 | 6 | 6 | 13 |
| Overall evaluation | D | D | C | B | C | B | B | C |
| Note | Comparative Example | Comparative Example | Example | Example | Example | Example | Example | Example |

|  | Experimental Example 9 | Experimental Example 10 | Experimental Example 11 | Experimental Example 12 | Experimental Example 13 | Experimental Example 14 | Experimental Example 15 |
|---|---|---|---|---|---|---|---|
| Farthest horizontal distance (μm) | 450 | 450 | 450 | 30 | 100 | 450 | 30 |
| Nearest horizontal distance (μm) | 150 | 150 | 150 | 5 | 20 | 150 | 5 |
| Average distance (μm) | 300 | 300 | 300 | 17.5 | 60 | 300 | 17.5 |
| Colored latex particle diameter (μm) | 5 | 20 | 100 | 0.5 μm and 1 μm were mixed in equal volumes | 1 μm and 5 μm were mixed in equal volumes | 5 μm and 20 μm were mixed in equal volumes | 0.4 |
| Diameter of convex portion (μm) | 300 | 300 | 300 | 25 | 80 | 300 | 25 |
| Height of convex portion (μm) | 450 | 450 | 450 | 30 | 100 | 450 | 30 |
| Maximum visible-determination allowable dilution rate of type A | $5 \times 10^4$ | $6 \times 10^4$ | $7 \times 10^4$ | $7 \times 10^4$ | $8 \times 10^4$ | $8 \times 10^4$ | $3 \times 10^4$ |
| Maximum visible-determination allowable dilution rate of type B | $5 \times 10^3$ | $6 \times 10^3$ | $7 \times 10^3$ | $7 \times 10^3$ | $8 \times 10^3$ | $8 \times 10^3$ | $3 \times 10^3$ |
| Detection time | 7 | 7 | 15 | 7 | 6 | 7 | 7 |
| Overall evaluation | B | B | C | A | A | A | D |
| Note | Example | Example | Example | Example | Example | Example | Comparative Example |

"—" represents "unable to measure"

TABLE 2

|  | Experimental Example 16 | Experimental Example 17 | Experimental Example 18 | Experimental Example 19 | Experimental Example 20 | Experimental Example 21 | Experimental Example 22 | Experimental Example 23 | Experimental Example 24 | Experimental Example 25 | Experimental Example 26 | Experimental Example 27 |
|---|---|---|---|---|---|---|---|---|---|---|---|---|
| Farthest horizontal distance (μm) | 30 | 30 | 30 | 100 | 100 | 100 | 450 | 450 | 450 | 30 | 100 | 450 |
| Nearest horizontal distance (μm) | 5 | 5 | 5 | 20 | 20 | 20 | 150 | 150 | 150 | 5 | 20 | 150 |

TABLE 2-continued

| | Experimental Example 16 | Experimental Example 17 | Experimental Example 18 | Experimental Example 19 | Experimental Example 20 | Experimental Example 21 | Experimental Example 22 | Experimental Example 23 | Experimental Example 24 | Experimental Example 25 | Experimental Example 26 | Experimental Example 27 |
|---|---|---|---|---|---|---|---|---|---|---|---|---|
| Average distance (μm) | 17.5 | 17.5 | 17.5 | 60 | 60 | 60 | 300 | 300 | 300 | 17.5 | 60 | 300 |
| Fluorescent latex particle diameter (μm) | 0.5 | 1 | 5 | 1 | 5 | 20 | 5 | 20 | 100 | 0.5 μm and 1 μm were mixed in equal volumes | 1 μm and 5 μm were mixed in equal volumes | 5 μm and 20 μm were mixed in equal volumes |
| Diameter of convex portion (μm) | 25 | 25 | 25 | 80 | 80 | 80 | 300 | 300 | 300 | 25 | 80 | 300 |
| Height of convex portion (μm) | 30 | 30 | 30 | 100 | 100 | 100 | 450 | 450 | 450 | 30 | 100 | 450 |
| Maximum fluorescent-determination allowable dilution rate of type A 10 minutes after initiation of test | $2 \times 10^5$ | $3 \times 10^5$ | $1 \times 10^5$ | $3 \times 10^5$ | $4 \times 10^5$ | $2 \times 10^5$ | $3 \times 10^4$ | $4 \times 10^4$ | $2 \times 10^5$ | $5 \times 10^5$ | $6 \times 10^5$ | $6 \times 10^5$ |
| Maximum fluorescent-determination allowable dilution rate of type B 10 minutes after initiation of test | $2 \times 10^4$ | $3 \times 10^4$ | $1 \times 10^4$ | $3 \times 10^4$ | $4 \times 10^4$ | $2 \times 10^4$ | $3 \times 10^3$ | $4 \times 10^3$ | $2 \times 10^4$ | $5 \times 10^4$ | $6 \times 10^4$ | $6 \times 10^4$ |
| Overall evaluation | C | B | C | B | B | C | B | B | C | A | A | A |
| Note | Example | Example | Example | Example | Example | Example | Example | Example | Example | Example | Example | Example |

From the results shown in Tables 1 to 2, it was demonstrated that the liquid sample test kit according to the embodiment enables highly sensitive detection by specifying the size of microstructures in the flow path and developing a label in accordance with the size. If the diameter of the particle is small, dilution limit becomes low and sensitivity is low (Experimental Example 1, Experimental Example 15). If the diameter of the particle is large, a label cannot be developed and detection cannot be made (Experimental Example 2).

INDUSTRIAL APPLICABILITY

In the embodiment, in an immunochromatography, which enables optical confirmation that a target substance was detected, a test kit that enables highly sensitive determination is provided. The liquid sample test kit according to the embodiment enables implementation of a highly sensible test at low cost and is thus useful as a disposable POCT reagent.

REFERENCE SIGNS LIST

2: Flow path, 3: Membrane carrier having microstructures provided therein, 3x: Drop zone, 3y: Detection zone, 4,4a, 4b,4c,4d,4e: Representative length of the bottom surface of a convex portion (diameter of convex-portion bottom), 5A: Farthest horizontal distance between adjacent microstructures (nearest center-to-center distance), 5B: Nearest horizontal distance between the adjacent microstructures (distance between the most proximate microstructures), 5C: Distance of the space between adjacent microstructures, 6,6a,6b,6c,6d: Height of convex portions, 7,7a,7b,7c,7d,7e: Microstructure, 8,8a,8b,8c,8d,8e: Convex portion, 9: Flat part, 10,10a,10b,10c,10d: Bottom surface of convex portions, 18: Test kit for liquid sample, 18a: Case, 18b: First opening, 18c: Second opening, d: Liquid sample flow direction (transport direction)

The invention claimed is:

1. A membrane carrier comprising a flow path, and a detection zone for detecting a target substance, wherein
a microstructure is formed at a bottom of the flow path, wherein the microstructure comprises a plurality of convex portions, wherein each of the plurality of convex portions has a height of 10 μm to 500 μm and a bottom diameter of 10 μm to 1,000 μm, and
a label, which comprises a particle to which an antibody or an antigen binds, is arranged in at least a part of the flow path and is able to bind to the target substance and be transported to the detection zone, the particle having a diameter in the range of 500 nm to 100,000 nm, and
a detection substance immobilized on the detection zone, the detection substance able to bind to a compound comprising the target substance bound to the label.

2. The membrane carrier according to claim 1, wherein an average horizontal distance between adjacent convex portions is at least 3 times the diameter of the particle and is 300 μm or less.

3. The membrane carrier according to claim 1, wherein the particle is one or more selected from the group consisting of a colored latex particle and a fluorescent latex particle.

4. The membrane carrier according to claim 1, wherein the membrane carrier is a membrane carrier for a test kit of detecting a target substance in a liquid sample, and the antibody and antigen specifically react with a target substance in the liquid sample.

5. The membrane carrier according to claim 1, wherein the detection zone produces a color change when the target substance is detected.

6. A method for manufacturing a liquid sample test kit, comprising immobilizing a detection substance producing a color change by holding the target substance in the detection zone of the membrane carrier according to claim 5.

7. A liquid sample test kit comprising the membrane carrier according to claim 1.

* * * * *